United States Patent [19]
Kameyama

[11] Patent Number: 5,527,260
[45] Date of Patent: Jun. 18, 1996

[54] METHOD FOR FREEZING BOVINE EMBRYOS

[75] Inventor: Kenji Kameyama, Ibaraki-ken, Japan

[73] Assignee: National Federation of Agricultural Cooperative Associations, Tokyo, Japan

[21] Appl. No.: 284,176

[22] Filed: Aug. 2, 1994

[30] Foreign Application Priority Data

Feb. 3, 1994 [JP] Japan .................................. 6-011602

[51] Int. Cl.⁶ .................................................. A61B 17/43
[52] U.S. Cl. ........................................ 600/33; 128/898
[58] Field of Search .................. 600/33–35; 128/897–98

[56] References Cited

U.S. PATENT DOCUMENTS

| | | | |
|---|---|---|---|
| 4,380,997 | 4/1983 | Leibo | 600/34 |
| 4,512,337 | 4/1985 | Leveskis | 600/34 |
| 5,160,312 | 11/1992 | Voelkez | 600/34 |

FOREIGN PATENT DOCUMENTS

| | | | |
|---|---|---|---|
| 2546755 | 12/1984 | France | 600/33 |
| 1138149 | 2/1985 | U.S.S.R. | 600/33 |
| 1331499 | 8/1987 | U.S.S.R. | 600/33 |
| 1521474 | 11/1989 | U.S.S.R. | 600/33 |
| 1782568 | 12/1992 | U.S.S.R. | 600/34 |

OTHER PUBLICATIONS

K. R. Bondioli et al., "The Use of male–Specific Chromosomal DNA Fragments to Determine the Sex of Bovine Preimplantation Embryos", Theriogenology, Jan. 1989, vol. 31, No. 1, pp. 95–104.

M. Nibart et al., "Rapid Bovine Embryo Sexing by DNA Probe: Field Results", 12th ICAR, No. 212, pp. 727–729, 1992.

C. M. Herr et al., "Micromanipulation of Bovine Embryos for Sex Determination", Theriogenology, Jan. 1991, vol. 35, No. 1, pp. 45–54.

*Primary Examiner*—Angela D. Sykes
*Assistant Examiner*—J. P. Lacyk
*Attorney, Agent, or Firm*—Foley & Lardner

[57] ABSTRACT

A method for freezing bovine embryos which comprises adding a dextran and supplemented calf serum to bovine embryos, and freezing the resulting mixture.

21 Claims, 1 Drawing Sheet

METHOD FOR FREEZING BOVINE EMBRYOS

BACKGROUND OF THE INVENTION

The present invention relates to a method for freezing bovine embryos. More particularly, the present invention relates to a method for freezing bovine embryos obtained by in vivo or in vitro fertilization, or bovine embryos subjected to biopsy for gene diagnosis or chromosome analysis.

DESCRIPTION OF THE PRIOR ART

In a step-wise method conventionally employed for freezing bovine embryos, frozen embryos are thawed and then a cryoprotectant is removed under a microscope. This method requires not only a fairly long time and much labor after the thawing but also a microscope. Therefore, a more convenient method is desired in working sites. The conception rate in the aforesaid method is 50 to 60%. Furthermore, when this method is applied to embryos freed from zona pellucida by biopsy, the conception rate is decreased to 30 to 40% (Bondioli et al., Theriogenology, 31, 95–104, 1989; Nibart et al., 12th ICAR, Abstract No. 212, 727–729, 1992).

There have come to be carried out gene examinations, for example, sexing of embryos by a PCR method which is now expected to be most practical. For investigating the genes of embryos, biopsy of the embryos is indispensable. A large hole is formed in the zona pellucida by the biopsy, so that the zona pellucida is completely or substantially removed. When the embryos thus lose the zona pellucida, their cryopreservation becomes difficult in practice.

In addition, there is a method (a step-wise method in which a dextran is added in an amount of 10%) which gives such a good result that the conception rate of embryos subjected to biopsy for sexing (embryos freed from zona pellucida) is 63.0% ($17/27$) (Herr & Reed, Theriogenology, 35, 45–54, 1991). But, the present inventor examined this method to find that this method tends to give different results, depending on developmental stage. Moreover, this method is not a direct method and hence cannot be widely generalized. Accordingly, the present invention was made.

SUMMARY OF THE INVENTION

The present invention is a method for freezing bovine embryos in which a dextran and supplemented calf serum are added to bovine embryos. According to this method, a fairly high conception rate can be attained even in transplantation of embryos subjected to biopsy. Furthermore, this method is a simple method which permits direct transfer into recipients after thawing. Needless to say, a higher conception rate can be attained in the case of embryos not subjected to biopsy.

DESCRIPTION OF THE PREFERRED EMBODIMENTS

Figure 1:
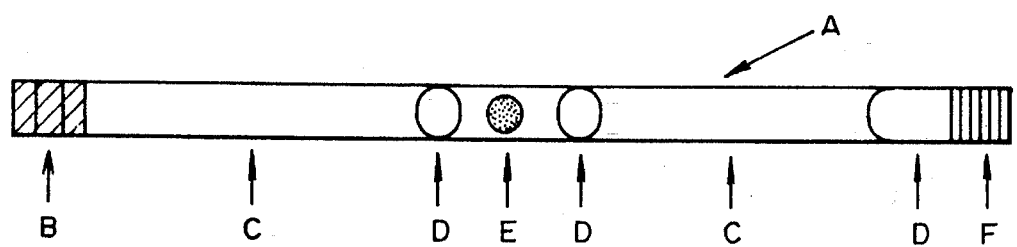
FIG. 1 shows a cross-sectional view of a straw enclosing an embryo according to the present invention. The main body of the straw (A), cotton plug (B), solution to be frozen (C), air (D), solution to be frozen and embryo (E), and seal (F) are shown in the FIGURE.

The present invention is further illustrated with the following examples.

EXAMPLE 1

(1) Solution to be frozen:

The composition of a solution to be frozen which was directly transferable into recipients and was prepared by adding supplemented calf serum (or a material obtained by adding the same growth factors and trace elements as described below to bovine fetal serum or the like) and a dextran to a cryoprotectant, was as follows:

4% (v/v) ethylene glycol

4% (v/v) propelene glycol

20% (v/v) supplemented calf serum *

1% (v/V) dextran ** base medium: DPBS (Dulbecco's phosphate buffer solution)

* adjusted serum containing insulin, transferrin, trace elements and other growth factors (available from Gibco).
** high-molecular weight polysaccharide formed mainly by α-1,6 linkages which has a molecular weight of 10,000 to 2,000,000. A dextran having an average molecular weight of 500,000 was used in the present example.

(2) Container for freezing:

a 0.25-ml plastic straw (3) Method for insertion into the straw:

As shown in FIG. 1, the following were inserted so as to be located in the numerical order from the cotton plug end in the straw.
1. the solution to be frozen
2. air
3. the solution to be frozen and embryos
4. air
5. the solution to be frozen (4) Program freezer: manufactured by Tokyo Rika (5) Ice seeding temperature: −6° C.

(6) Cooling rate: 0.5° C./min (7) Temperature at the immersion in liquid nitrogen: −32.5° C.

(8) Thawing method:

The straw was taken out of liquid nitrogen, held in air (at room temperature) for 5 to 10 seconds, and then thawed in warm water at 35° C.

(9) Method for recovering and cultivating embryos in a cultivation test:

The whole contents of the straw were introduced in DPBS+0.2M sucrose+10% calf serum and the mixture was allowed to stand for 5 minutes. Thereafter, the embryos were cultured for 48 hours together with bovine granulosa cells by using TCM 199 medium+5% supplemented calf serum.

(10) Transplantation method in a transplantation test:

The straw was set in a transplanter as it was, followed by transplantation.

TABLE 1

| | Freezing and thawing method (Comparison with a conventional method) | |
|---|---|---|
| Method | Freezing solution | Thawing method |
| Conventional method (SW method*) | 10% Glycerol + 0.4% BSA | 3 steps (6.7%, 3.3%, 0%, Glycerol + 0.3M sucrose + 0.4% BSA) |
| Method of the invention | 4% Ethylene glycol + 4% propylene glycol + 20% supplemented calf serum + 1% dextran | Direct transplantation |

*step-wise method as prior art

TABLE 2-1

Freezing test on bovine embryos obtained by
in vitro fertilization (cultivation results)

| Freezing and thawing method | n | 2 Hours after thawing Number of surviving embryos | 2 Hours after thawing Number of transferable embryos | 48 hours after thawing Number of hatched embryos |
|---|---|---|---|---|
| SW method | 7 | 7 (100%) | 0 (0.0%) | 3 (42.9%) |
| Method of the invention | 12 | 12 (100%) | 2 (16.7%) | 6 (50.0%) |

TABLE 2-2

Freezing test on bovine embryos freed
from zona pellucida (cultivation results)

| Freezing and thawing method | n | 2 Hours after thawing Number of surviving embryos | 2 Hours after thawing Number of transferable embryos |
|---|---|---|---|
| SW method | 20 | 5 (25.5%) | 0 (0.0%) |
| Method of the invention | 11 | 10 (90.9%) | 5 (45.5%) |

TABLE 3

Freezing test on bovine embryos freed from
zona pellucida (transplantation results)

| Freezing and thawing method | n | Number of implanted embryos |
|---|---|---|
| SW method | 24 | 2 (8.3%) |
| Method of the invention | 20 | 13 (61.9%) |

*The implantation of embryos was confirmed by ultrasonic diagnosis 60 days after the estrus of recipients (the most usual number of days at which implantation is confirmed).

As is clear from the above, as compared with the conventional method, the method of the present invention gave better results in all of the cultivation tests on embryos obtained by in vitro fertilization and embryos freed from zona pellucida and the transplantation test on the embryos freed from zona pellucida (Tables 1 to 3). Particularly in the case of the transplantation results shown in Table 3, there could be obtained a conception rate of 61.9% ($^{13}/_{20}$) which is equal to the usual conception rate of frozen bovine embryos and is the best result for embryos subjected to biopsy.

It can be conjectured that dextrans accelerate the dehydration of cells and that since they increase the viscosity of a solution, they are effective in protecting the cell surface of, in particular, embryos which have lost their zona pellucidas. The above-mentioned method of Herr et al. uses a characteristic solution to be frozen which has a very high viscosity because it contains a dextran in an amount of as much as 10%. Thus, it can be speculated that owing to such a solution to be frozen, different results are obtained depending on developmental stage (bad results are obtained in the case of enlarged blastocysts having an enlarged blastocoel). In addition, the concentration of 10% gives too high a viscosity, so that sterilization by filtration becomes difficult. Even when the concentration was 5%, it was necessary to change the poresize and the filtration area.

EXAMPLE 2

For investigating the optimum concentration of dextran, a test was carried out according to the methods described in Example 1. As can be seen from the results shown below, a desirable tendency was observed in the growth of the 1% group.

TABLE 4-1

Freezing test on bovine embryos
obtained by in vitro fertilization

| Dextran concentration (v/v) | n | 2 Hours after thawing Number of surviving embryos | 2 Hours after thawing Number of transferable embryos | 48 Hours after thawing Number of hatched embryos |
|---|---|---|---|---|
| 0% | 21 | 18 (85.7%) | 3 (14.3%) | 4 (19.0%) |
| 1%* | 21 | 17 (81.0%) | 3 (14.3%) | 9 (42.9%) |
| 5% | 14 | 9 (64.2%) | 0 (0.0%) | 3 (21.4%) |

*This group corresponds to the present invention.

TABLE 4-2

Freezing test on bovine embryos
freed from zona pellucida

| Dextran concentration (v/v) | n | 2 Hours after thawing Number of surviving embryos | 2 Hours after thawing Number of transferable embryos | 48 Hours after thawing Number of growing embryos |
|---|---|---|---|---|
| 0% | 9 | 6 (66.7%) | 2 (22.2%) | 3 (33.3%) |
| 1%* | 9 | 7 (77.7%) | 4 (44.4%) | 5 (55.6%) |
| 5% | 9 | 8 (88.9%) | 1 (11.0%) | 3 (33.3%) |

*This group corresponds to the present invention.

EXAMPLE 3

There was carried out a test for comparing dextran with sucrose and trehalose which are often used as non-penetrable cryoprotectants.

TABLE 5

Freezing test on bovine embryos
obtained by in vitro fertilization

| Additives | n | 2 Hours after thawing Number of surviving embryos | 2 Hours after thawing Number of transferable embryos | 48 Hours after thawing Number of hatched embryos |
|---|---|---|---|---|
| — | 21 | 18 (85.7%) | 3 (14.3%) | 4 (19.0%) |
| Sutrose | 20 | 18 (85.7%) | 2 (10.0%) | 7 (35.0%) |
| Trehalose | 21 | 17 (81.0%) | 2 (9.5%) | 5 (23.8%) |
| Dextran | 21 | 17 (81.0%) | 3 (14.3%) | 9 (42.9%) |

The concentration of each additive was 1% (v/v). The dextran group corresponds to the present invention.

EXAMPLE 4

There was carried out a test for comparing supplemented calf serum with BSA (bovine serum albumin) and calf serum.

TABLE 6

Freezing test on bovine embryos obtained by in vitro fertilization

| Additives | n | 2 Hours after thawing | | 48 Hours after thawing |
|---|---|---|---|---|
| | | Number of surviving embryos | Number of transferable embryos | Number of hatched embryos |
| BSA | 12 | 9 (75.0%) | 1 (8.3%) | 5 (41.7%) |
| Calf serum | 12 | 10 (83.3%) | 3 (25.0%) | 5 (41.7%) |
| Supplemented Calf serum* | 21 | 17 (81.0%) | 8 (38.1%) | 9 (42.9%) |

*Corresponding to the method of the present invention.

TABLE 6-2

Freezing test on bovine embryos freed from zone pellucida

| Additives | n | 2 Hours after thawing | | 48 Hours after thawing |
|---|---|---|---|---|
| | | Number of surviving embryos | Number of transferable embryos | Number of hatched embryos |
| BSA | 9 | 9 (100%) | 4 (44.4%) | 3 (33.3%) |
| Calf serum | 9 | 8 (88.9%) | 3 (33.3%) | 3 (33.3%) |
| Supplemented Calf serum* | 9 | 7 (77.8%) | 4 (44.4%) | 5 (55.6%) |

*Corresponding to the method of the present invention.

The terms used in the above tables are explained below.

The term "bovine embryos freed from zona pellucida" means embryos (at a stage of morula or blastocyst 7 to 8 days after fertilization) collected from a live cow, from which the zona pellucida has been removed by biopsy or binary splitting.

The term "bovine embryos obtained by in vitro fertilization" means embryos at the early stage to a stage of enlarged blastocyst 7 days after in vitro fertilization.

The term "surviving embryos 2 hours after thawing" means embryos whose survival was confirmed regardless of their quality.

The term "transferable embryos 2 hours after thawing" means embryos among surviving embryos, which were judged to be so good in quality that they were transferable.

The term "growing embryos 48 hours after thawing" means embryos showing satisfactory growth by cultivation.

The term "hatched embryos 48 hours after thawing" means embryos hatched by (in vitro culture).

I claim:

1. A method for freezing a bovine embryo which comprises
   providing a bovine embryo,
   adding a dextran and supplemented calf serum to said bovine embryo, wherein said supplemented calf serum comprises insulin and transferrin, and
   freezing the resulting mixture.

2. A method according to claim 1, wherein said provided bovine embryo is one that has lost its zona pellucida.

3. A method according to claim 1, wherein the concentration of the dextran is about 1%.

4. A method according to claim 1, wherein the concentration of the supplemented calf serum is about 20%.

5. A method according to claim 1, wherein said provided bovine embryo is one that has been obtained by in vivo fertilization.

6. A method according to claim 1, wherein said provided bovine embryo one that has been subjected to biopsy.

7. A method according to claim 1, wherein said dextran has a molecular weight of from 10,000 to 2,000,000.

8. A method for transplanting a bovine embryo frozen in accordance with claim 1 into a recipient, comprising
   thawing the mixture of frozen bovine embryo, dextran and supplemented calf serum, and
   transferring said mixture into said recipient.

9. A method according to claim 8, wherein said provided bovine embryo is one that has lost its zona pellucida.

10. A method according to claim 1, wherein said provided bovine embryo is one that has been obtained by in vitro fertilization.

11. A frozen bovine embryo mixture comprising a bovine embryo, dextran and supplemented calf serum, wherein said supplemented calf serum comprises insulin and transferrin.

12. A mixture according to claim 11, wherein said bovine embryo is one that has lost its zona pellucida.

13. A mixture according to claim 11, wherein said dextran has a molecular weight of from 10,000 to 2,000,000.

14. A mixture according to claim 11, wherein said bovine embryo is one that has been obtained by in vivo fertilization.

15. A mixture according to claim 11, wherein said provided bovine embryo is one that has been obtained by in vitro fertilization.

16. A method for cultivating a bovine embryo frozen in accordance with claim 1, comprising
   thawing said mixture of frozen bovine embryo, dextran and supplemented calf serum,
   introducing said mixture into a phosphate buffer solution comprising 0.2M sucrose and 10% calf serum, and
   culturing said bovine embryo with bovine granulosa cells.

17. A method according to claim 16, wherein said provided bovine embryo is one that has lost its zona pellucida.

18. A method according to claim 16, wherein said supplemented calf serum comprises insulin and transferrin.

19. A method according to claim 16, wherein said dextran has a molecular weight of from 10,000 to 2,000,000.

20. A method according to claim 16, wherein said provided bovine embryo is one that has been obtained by in vivo fertilization.

21. A method according to claim 16, wherein said provided bovine embryo is one that has been obtained by in vitro fertilization.

* * * * *